(12) United States Patent
Payton et al.

(10) Patent No.: US 8,453,641 B2
(45) Date of Patent: Jun. 4, 2013

(54) APPARATUS FOR MEASURING PROPERTIES OF GASES SUPPLIED TO A PATIENT

(75) Inventors: Matthew Jon Payton, Auckland (NZ); Kevin Peter O'Donnell, Auckland (NZ); Andrew Baden Clark, Auckland (NZ); Christopher Simon Jams Quill, Auckland (NZ); Peter Geoffrey Hawkins, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1157 days.

(21) Appl. No.: 11/572,822

(22) PCT Filed: Aug. 19, 2005

(86) PCT No.: PCT/NZ2005/000219
§ 371 (c)(1), (2), (4) Date: Oct. 18, 2007

(87) PCT Pub. No.: WO2006/019323
PCT Pub. Date: Feb. 23, 2006

(65) Prior Publication Data
US 2008/0028850 A1 Feb. 7, 2008

(30) Foreign Application Priority Data
Aug. 20, 2004 (NZ) ........................................ 534853

(51) Int. Cl.
*A61M 11/00* (2006.01)
(52) U.S. Cl.
USPC ..................................................... 128/204.17
(58) Field of Classification Search
USPC ............. 128/204.17, 203.17, 205.23, 202.22, 128/204.21, 204.22, 204.18; 261/129, 131, 261/142, DIG. 65
See application file for complete search history.

(56) References Cited

U.S. PATENT DOCUMENTS

| 4,686,354 A | 8/1987 | Makin |
| 4,695,955 A | 9/1987 | Faisandier |
| 5,230,331 A | 7/1993 | Rusz et al. |

(Continued)

FOREIGN PATENT DOCUMENTS

| CN | 1370085 A | 9/2002 |
| DE | 4020522 A1 | 1/1992 |

(Continued)

OTHER PUBLICATIONS

Chinese Examination Report of CN Application No. 200580028386. 6; with English Translation of Pertinent Portion, dated Apr. 12, 2012; 8 pages.

(Continued)

*Primary Examiner* — Steven Douglas
(74) *Attorney, Agent, or Firm* — Knobbe, Martens, Olson & Bear, LLP

(57) ABSTRACT

The gases temperature supplied to a patient when the patient is undergoing treatment such as oxygen therapy or positive pressure treatment for conditions such as Obstructive Sleep Apnea (OSA) or Chronic Obstructive Pulmonary Disease (COPD) is often measured for safety and to enable controlling of the humidity delivered to the patient. The invention disclosed is related to measurement of properties, particularly temperature (thermister 23), of gases flowing through a heated tube (3), supplying gases to a patient, which utilizes the heating wire (21, 28) within the tube.

30 Claims, 4 Drawing Sheets

U.S. PATENT DOCUMENTS

| | | | |
|---|---|---|---|
| 6,078,730 | A | 6/2000 | Huddart et al. |
| 6,109,782 | A | 8/2000 | Fukura et al. |
| 6,167,833 | B1 | 1/2001 | Caraway et al. |
| 6,272,933 | B1 | 8/2001 | Gradon et al. |
| 6,584,972 | B2 | 7/2003 | McPhee |
| 6,694,974 | B1 | 2/2004 | George-Gradon et al. |
| 7,588,186 | B2 | 9/2009 | Steffen et al. |
| 8,063,343 | B2 | 11/2011 | McGhin et al. |
| 2002/0038392 | A1 | 3/2002 | De La Huerga |
| 2003/0079748 | A1* | 5/2003 | Seakins .................... 128/203.17 |
| 2003/0154977 | A1* | 8/2003 | White et al. ............. 128/203.26 |
| 2004/0074495 | A1 | 4/2004 | Wickham et al. |

FOREIGN PATENT DOCUMENTS

| | | |
|---|---|---|
| DE | 19647548 A1 | 5/1998 |
| DE | 202 02 906 | 2/2002 |
| EP | 1579984 A1 | 9/2005 |
| GB | 2 173 274 | 10/1986 |
| WO | WO 9221163 | 11/1992 |
| WO | 2004/105848 | 12/2004 |
| WO | 2005/021076 | 3/2005 |
| WO | WO 2006/092001 | 9/2006 |

OTHER PUBLICATIONS

Chinese Examination Report; Cover letters dated Jul. 19, 2011 and Aug. 12, 2011 with English translation of pertinent portions of examination report; 9 pages.

Canadian Examination Report, dated Mar. 31, 2011, 2 pages.

Canadian Office Action; dated Nov. 1, 2012; 2 pages.

* cited by examiner

APPARATUS FOR MEASURING PROPERTIES OF GASES SUPPLIED TO A PATIENT

This application is a National Phase filing of PCT/NZ2005/000219, having an International filing date of Aug. 19, 2005, which claims priority of NZ534853 having a filing date of Aug. 20, 2004.

TECHNICAL FIELD

This invention relates to an apparatus for measuring properties, such as temperature and humidity, of gases being supplied to a patient. Humidifiers are commonly controlled by measuring the temperature of gas at two points, adjacent to the output of the humidifier and proximal to the patient. This invention predominantly relates to the measurement of temperature of gas supplied to a patient at a point proximal to the patient.

BACKGROUND ART

The gases temperature supplied to a patient when the patient is undergoing treatment such as oxygen therapy or positive pressure treatment for conditions such as Obstructive Sleep Apnea (OSA) or Chronic Obstructive Pulmonary Disease (COPD) is often measured for safety and to enable controlling of the humidity delivered to the patient. Measurement of temperature near the patient is commonly performed using a probe inserted into the breathing tube, such as that of Fisher & Paykel Healthcare Limited, U.S. Pat. Nos. 6,272,933 and 6,584,972. Such a temperature probe is connected to the humidifier through a cable that runs external to the breathing circuit This approach has some drawbacks. In particular, the user must correctly install the temperature probe. If the probe is not correctly installed then the humidification system may malfunction which may increase risk to the patient. Existing end of breathing tube sensors require sensor wires to be run down the outside of the breathing tube. This lowers reliability of the sensors due to the vulnerability of these wires. Alternatively, if these wires are run down the inside of the breathing tube there would be an increase of the resistance to airflow and the hygiene of the breathing circuit would be lowered.

DISCLOSURE OF THE INVENTION

It is an object of the present invention to provide a method of measuring properties of gases supplied to a patient that goes some way to overcoming the abovementioned disadvantages in the prior art or which will at least provide the industry with a useful choice.

Accordingly in a first aspect the present invention consists in an apparatus for measuring properties of gases being supplied to a patient comprising:
 a gases supply,
 at least one delivery conduit including a heater wire for heating said conduit,
 wherein said heater wire is utilised in an electrical circuit to determine said properties of said gases.

Preferably said electrical circuit is connected in series with said heater wire and provides a measurement or enables a calculation of an indication of at least one of temperature, humidity, pressure and composition of said gases.

Preferably said electrical circuit is mounted and sealed on a printed circuit board that at least partially extends into the gases supplied to said patient through said at least one delivery conduit.

Preferably said electrical circuit is at least partially moulded into the wall of said delivery conduit.

Preferably said electrical circuit includes a sensing means with known properties at ambient temperature such that said sensing means can be matched with said at least one delivery conduit.

Preferably said sensing means is a temperature sensor.

Preferably said electrical circuit includes at least one measuring means in series with said heater wire.

Preferably said at least measuring means is a temperature measuring means.

Preferably said temperature measuring means includes a thermistor and diode in parallel and a reference resistor.

Preferably said thermistor and said diode are located at the end of said delivery conduit near to said patient and said reference resistor is included in said gases supply means.

Preferably said gases supply means includes a device to supply gas flow, such as a blower, and a humidifier to humidify said gases from said blower.

Preferably said gases supply means is a humidifier.

Preferably said electrical circuit includes a gases property measuring means.

Preferably said gases property measuring means includes at least one of a sensor, band pass filter or thermistor and at least one reference resistor.

Preferably said at least one of a sensor, band pass filter or thermistor are located at the end of said delivery conduit near to said patient and said at least one reference resistor and at least one band pass filter is included in said gases supply means.

The invention consists in the foregoing and also envisages constructions of which the following gives examples.

BRIEF DESCRIPTION OF THE DRAWINGS

Preferred forms of the present invention will now be described with reference to the accompanying drawings.

BEST MODES FOR CARRYING OUT THE INVENTION

The present invention seeks to measure various properties, for example temperature or humidity, at the end of a gas delivery tube or conduit using sensors mounted on a wire, such as a wire used for heating the gases flow through the tube or conduit, where the wire resides within the delivery tube or conduit. A heated tube with a heating wire such as that described in Fisher & Paykel Healthcare Limited U.S. Pat. No. 6,078,730 or any other similar tube and heating wire could be utilised with the present invention.

Figure 1:
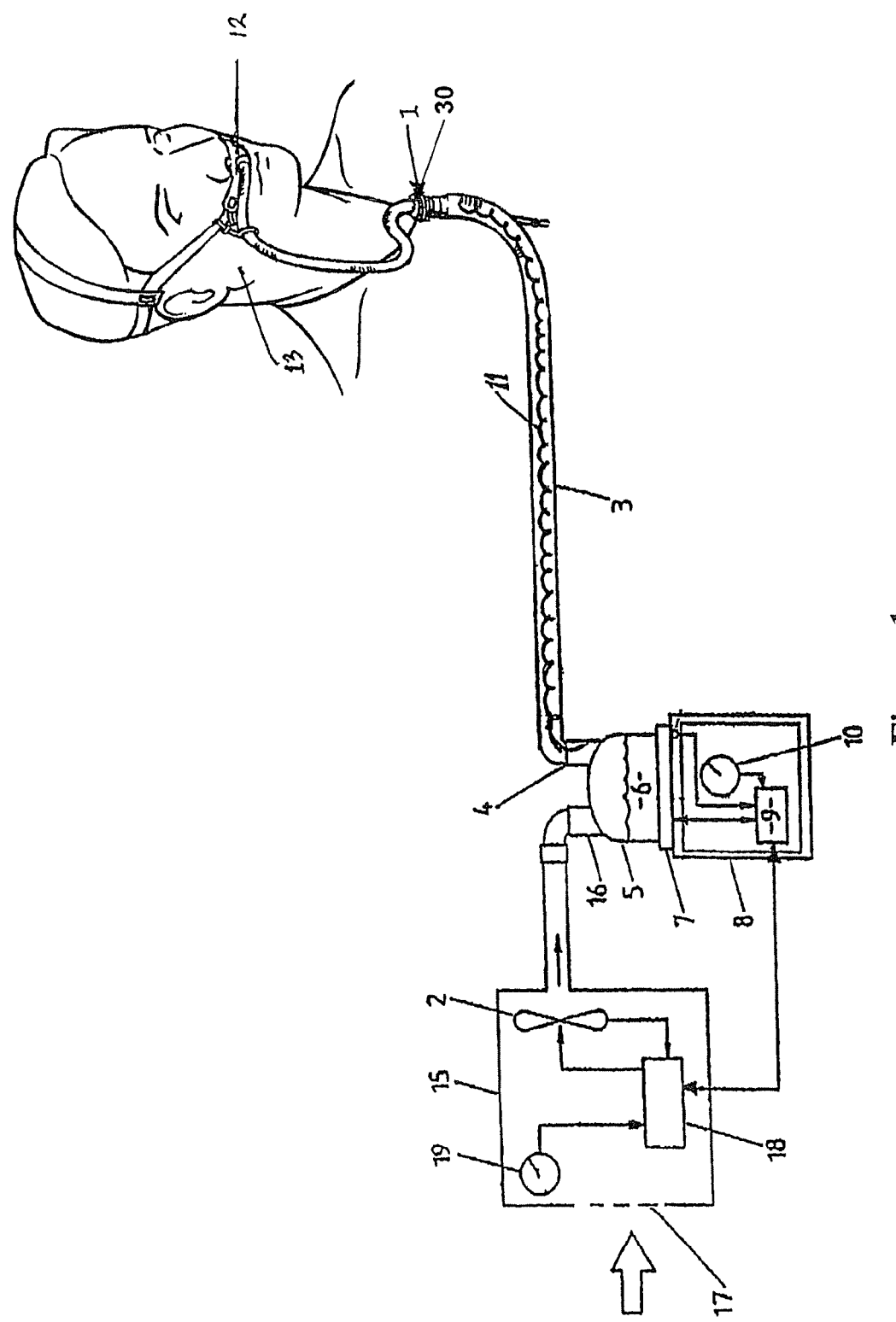
FIG. 1 is an illustration of a respiratory humidifier system that may be used with the method of the present invention of measuring temperature of gases supplied to a patient.

Referring to FIG. 1 a ventilation and humidifying system as might be used with the present invention is shown. A patient 13 is receiving humidified and pressurised gases through a nasal cannula 12 connected to a humidified gases transportation pathway or inspiratory conduit 3 that in turn is connected to a humidifier 8 (including humidification chamber 5) supplied with gases from a blower 15 or other appropriate gases supply means.

The inspiratory conduit 3 is connected to the outlet 4 of the humidification chamber 5 that contains a volume of water 6. The humidification chamber 5 is preferably formed from a plastics material and may have a highly heat conductive base (for example an aluminium base) that is in direct contact with a heater plate 7 of humidifier 8. The humidifier 8 is provided with control means or an electronic controller 9 that may comprise a microprocessor based controller executing computer software commands stored in associated memory. Gases flowing through the inspiratory conduit 3 are passed to the patient by way of the nasal cannula 12, but may also be passed to the patient by way of other patient interfaces such as a nasal or full face mask.

The controller 9 receives input from sources such as user input means or dial 10 through which a user of the device may, for example, set a predetermined required value (preset value) of humidity or temperature of the gases supplied to patient 13. In response to the user set humidity or temperature value input via dial 10 and other possible inputs such as internal sensors that sense gases flow or temperature, or by parameters calculated in the controller, controller 9 determines when (or to what level) to energize heater plate 7 to heat the water 6 within humidification chamber 5. As the volume of water 6 within humidification chamber 5 is heated, water vapour begins to fill the volume of the chamber above the surface of the water and is passed out of the humidification chamber 5 outlet 4 with the flow of gases (for example air) provided from a gases supply means or blower 15 which enters the humidification chamber 5 through inlet 16.

The blower 15 may be provided with a variable speed pump or fan 2 which draws air or other gases through the blower inlet 17. The speed of the variable speed pump or fan 2 may be controlled by a further control means or electronic controller 18 which responds either to inputs from controller 9 or to user-set predetermined required values (preset values) of pressure or fan speed, via dial 19. Alternatively, the function of this controller 18 can be combined with the other controller 9.

A heating element or wire 11 is preferably provided within, around and throughout the conduit or tubing 3 to help prevent condensation of the humidified gases within the conduit. Such condensation is due to the temperature of the walls of the conduit being close to the ambient temperature, (being the temperature of the surrounding atmosphere) which is usually lower than the temperature of the humidified gases within the conduit. The heater element effectively replaces the energy lost from the gases through conduction and convection during transit through the conduit. Thus the conduit heater element ensures the gases delivered are at an optimal temperature and humidity.

Such a heater wire is commonly driven either with direct current (DC) or alternating current (AC) and in both cases the heating voltage is usually switched on and off to control the power applied to the heating element. In the present invention the heating element 11, which is most preferably a wire, is used along with an electronic circuit to determine properties of the gases supplied to the patient. The circuit (20 or 40 in FIGS. 2 and 3) is preferably connected in series with the heater wire 11. The circuit may be on a printed circuit board, or wired within a housing that may be a plastic moulding in the gases flow, or a circuit board that is at least partially moulded within the wall of the conduit or tubing 3. The properties that may be measured include temperature, pressure, gas composition and humidity. Two embodiments of the present invention are described below, one that operates using only a DC heating voltage and the other that can operate with a DC or AC heating voltage.

DC Heating Voltage

Figure 2:
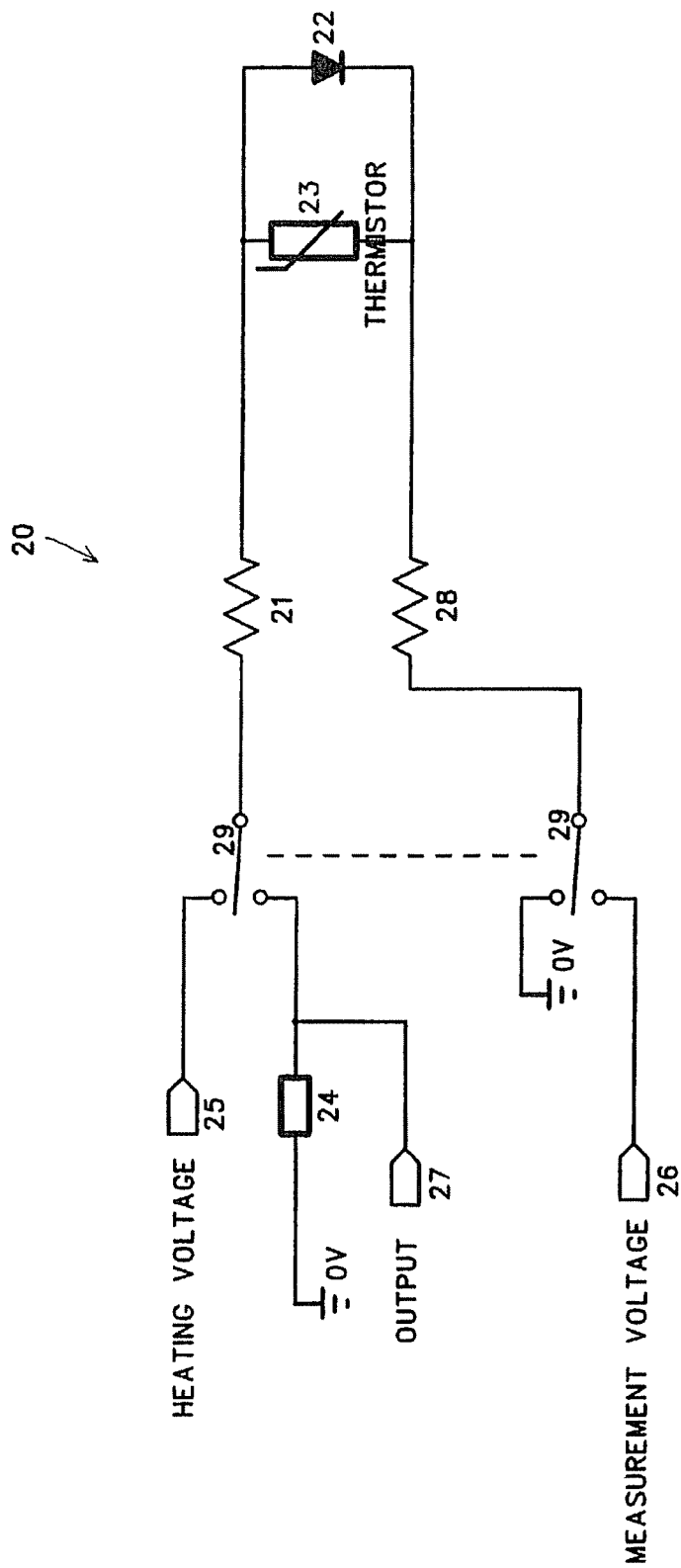
FIG. 2 is a circuit diagram of the electronics enabling the measurement of the temperature of gases to a patient, where the circuit is utilised when the system of the present invention is utilising DC heating and measuring voltages.

FIG. 2 shows a circuit 20 that may be utilised for carrying out the method of measuring temperature of the present invention. When a DC heating voltage 25 is applied to the heater wire the diode 22 conducts and current flows through the heater wire 21, 28 and the heater wire functions as normal and provides heating to the delivery tube 3. When the heating voltage 25 is switched off using switch 29, a measurement voltage 26, which has opposite polarity to the heating voltage 25 is applied to the heater wire. In this case, the current in the heater wire 21, 28 does not flow through the diode 22 but flows through the thermistor 23 and through a reference resistor 24. The voltage across the reference resistor 24 can then be measured at the output 27 and the temperature of the gases determined. The voltage measurement 27 across the reference resistor, 24, is converted to a temperature using a look up table or an equation to calculate a value for temperature. This is similar to a commonly used technique where the thermistor 23 forms a potential divider with the reference resistor 24.

More generally, the thermistor may be replaced by an impedance (for example, a resistor and a capacitive sensor) for pressure or humidity measurement. Either the impedance can be measured by measuring the voltage across the reference resistor 24 or the rise-time could be determined by looking at the voltage across the reference resistor 24 in time.

Figure 4:
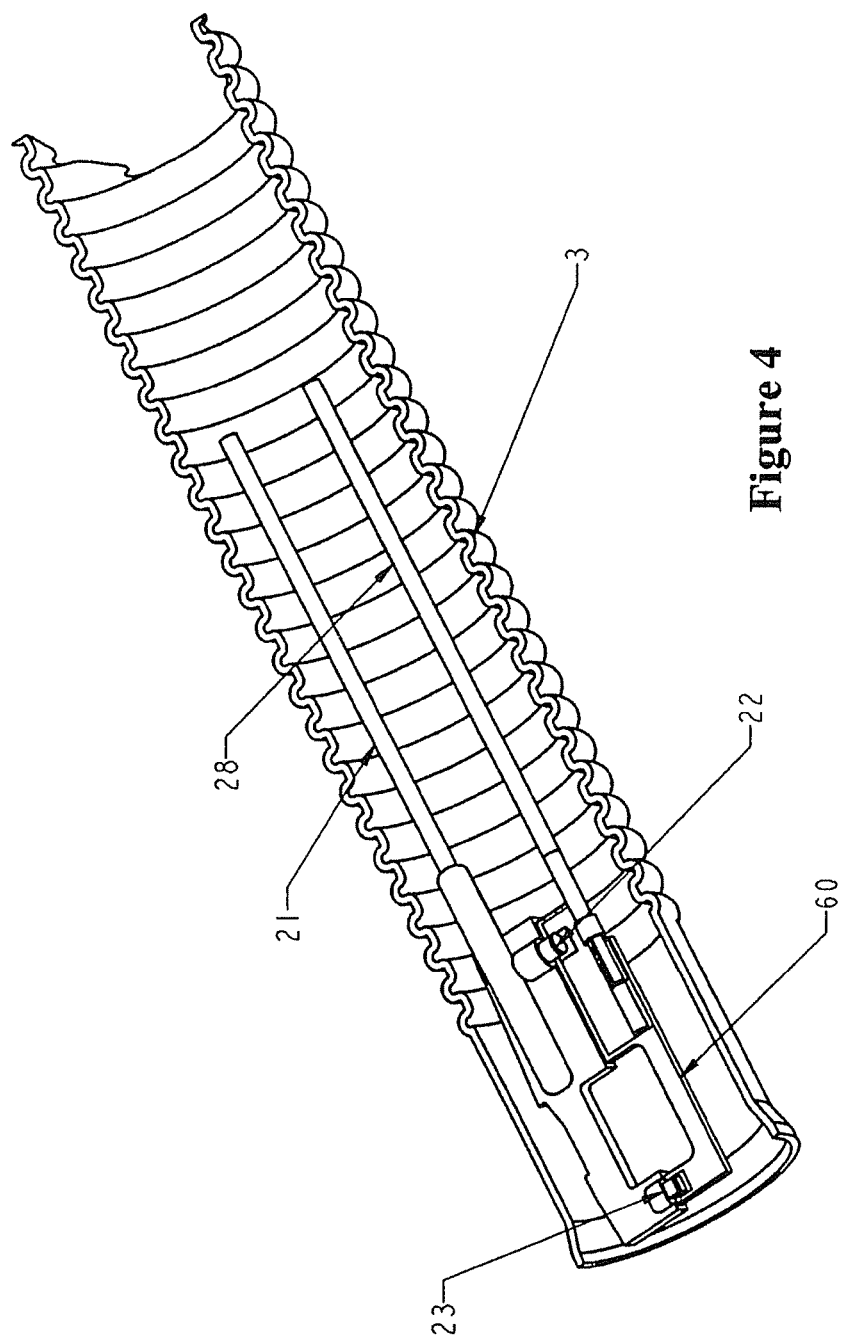
FIG. 4 is a cut away of a conduit including a circuit of the present invention on a printed circuit board and residing with the conduit in the area of gases flow.

Part of the circuit 20 would be included in the delivery conduit 3 and in particular the diode 22 and thermistor 23 (in parallel with one another) are preferably placed in series with the heater wire 21, 28 at a point in the heater wire at or near the end 30 (nearest the user 13, see FIGS. 1, 2 and 4) of the delivery tube 3, for example they may be interconnected on a printed circuit board, overmolded with plastic for sealing and mounted in the gases stream through the delivery conduit as shown in FIG. 4. Furthermore, the circuit may be formed by interconnected parts in a housing, for example, a plastic housing, that protrudes from the plastic wall of the delivery tube into the gases flow through the conduit, in order to measure that gases properties. All other parts of the circuit 20 including the reference resistor 24 and the switching circuitry 29 would be included in the control circuitry of the humidifier 8.

The thermistor's value can be chosen to have different resistance curves with known properties at ambient temperature. The choice of a particular thermistor value for use with the circuit allows identification by the control system of the present invention and matching of that thermistor value with a specific conduit or tubing 3. Such that different thermistor values can be matched with a particular and appropriate conduit types and upon connection of the conduit to a humidifier or blower device, the control system can identify that thermistor and apply the appropriate control strategy to the heating of the conduit.

AC or DC Heating Voltage

Figure 3:
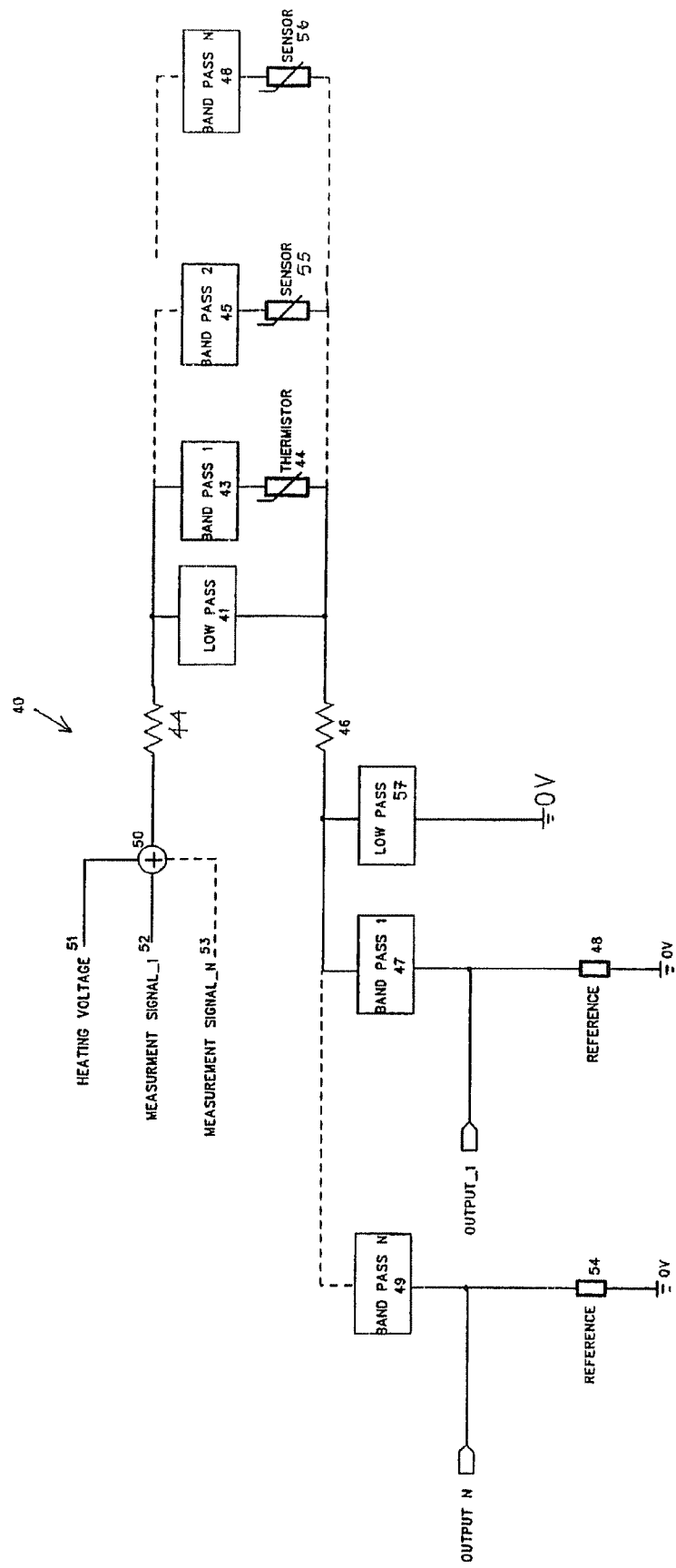
FIG. 3 is a circuit diagram of the electronics enabling the measurement of the temperature of gases to a patient, where the circuit is utilised when the system of the present invention is utilising DC or AC voltages for the heating and signal voltages.

The circuit shown in FIG. 2 is intended to be used when a DC heating voltage is used in conjunction with the heater wire, delivery conduit and system as shown in FIG. 1. An alternative embodiment of a circuit 40 that would provide measurement of the gases properties, such as temperature and is suitable for AC and DC voltages, is shown in FIG. 3. A number of voltage signals 51, 52, 53, which are at different frequencies, are added together at an adder 50. These signals include at least one heating signal 51 and at least one measuring signal 53. The combination of these signals passes down the heater wire 44, creating currents (heating and measuring) in the heater wire 44. A number of parallel paths are established 41, 43, 45 each containing a filter (for example, as shown in FIG. 3, one low pass filter 41 and three band pass filters 43, 45, 48) that each pass a different frequency range. These parallel paths (that is, filters, thermistors and/or sensors) are preferably located at the end 30 of the delivery tube 3, in a similar manner as described in relation to FIG. 2. The parallel paths allow the heating current to be passed through a different path to the measurement currents. It also allows multiple measurement signals to be passed through the heater wire so that different properties of the gases (e.g. temperature, pressure, humidity, composition) may be measured.

The heating and measurement currents return through the heater wire 46 and can be filtered through a number of measurement filters 47, 49, 57 in parallel that pass frequency bands that correspond to the filters, 41, 43, 45 located at the end 30 of the tube 3. The heating current takes a different path than the measurement currents. The measurement currents each take a different path depending on their frequency and this allows each measurement current to be measured by passing it through a reference resistor 48, 54 or similar. Again a look up table or equation may be used to convert the voltage across the reference resistor 48, 54 to, for example, a temperature. In the preferred embodiment of the present invention the measurement filters 47, 49, 57 would be included in the humidifier 8 control circuitry.

In a further embodiment one or more of the sensing elements 55, 56 at the end 30 of the delivery tube 3 could be replaced by a fixed impedance to allow identification of the tube so that different control algorithms can be used for different conduits or tubes.

FIG. 4 shows a cutaway view of a conduit 3 with a printed circuit board 60 housing the parts to one of the circuits of the present invention described above with reference to FIG. 2 or 3. The circuit board 60 is connected to the heating wires 21, 28 and as such is positioned within the conduit 3. In this manner, the thermistor 23 included on the board 60 is exposed to the gases flowing through the conduit 3 and can provide measurements of the properties of the gases.

The circuits and method of the present invention can be applied to a number of applications of these technologies for humidification and breathing circuit products. For example, the measurement of the temperature or humidity at the end of the delivery tube (or in a patient interface, for example, nasal cannula or mask) can be used to better control the humidifier, such that a more accurate temperature of gases can be supplied to the patient, providing optimal patient comfort and therapy. Additionally, other gases properties may be measured, such as the gases pressure or gas composition near the patient.

The apparatus of the present invention eliminates the need for external wires for sensing gases properties, as is required by the prior art. Furthermore the apparatus of the present invention only uses two pins or contacts (as opposed to four pins as used in current heated tube implementations). This means the system of the present invention is likely to be more reliable as the contacts/pins are likely to be less prone to breakage. The utilisation of the heater wire for measuring gases properties may also reduce the cost of the breathing tube 3 and associated parts, especially if the breathing tube is to be disposable.

The invention claimed is:

1. An apparatus for measuring properties of gases being supplied to a patient comprising:
    a gases supply,
    at least one delivery conduit including a heater wire for heating said conduit, said conduit having a first end nearest said gases supply and a second end furthest from said gases supply,
    wherein said heater wire is located within, around or throughout said conduit, said heater wire extending longitudinally along said conduit from at or near said first end of said conduit to at or near said second end of said conduit, and said heater wire being utilised in an electrical circuit to determine said properties of said gases, said electrical circuit having a first portion and a second portion, said first portion of said electrical circuit being located at or near said first end of said conduit and said second portion of said electrical circuit being located at or near said second end of said conduit, said second portion of said electrical circuit being in electrical communication with said first portion of said electrical circuit through said heater wire such that said first portion and said second portion of said electrical circuit through said heater wire can
    feedback to a controller when said properties of said gases vary.

2. An apparatus for measuring properties of gases being supplied to a patient according to claim 1 wherein said electrical circuit is connected in series with said heater wire and provides a measurement or enables a calculation of an indication of at least one of temperature, humidity, pressure and composition of said gases.

3. An apparatus for measuring properties of gases being supplied to a patient according to claim 1 wherein said second portion of said electrical circuit is mounted and sealed on a printed circuit board that at least partially extends into the gases supplied to said patient through said at least one delivery conduit.

4. An apparatus for measuring properties of gases being supplied to a patient according to claim 1 wherein said second portion of said electrical circuit is at least partially moulded into the wall of said delivery conduit.

5. An apparatus for measuring properties of gases being supplied to a patient according to claim 1 wherein said electrical circuit includes a sensor with known properties at ambient temperature such that said sensor can be matched with said at least one delivery conduit.

6. An apparatus for measuring properties of gases being supplied to a patient according to claim 5 wherein said sensor is a temperature sensor.

7. An apparatus for measuring properties of gases being supplied to a patient according to claim 1 wherein said electrical circuit includes at least one gas properties measuring component in series with said heater wire.

8. An apparatus for measuring properties of gases being supplied to a patient according to claim 7 wherein said at least one gas properties measuring circuit is a temperature measuring circuit.

9. An apparatus for measuring properties of gases being supplied to a patient according to claim 8 wherein said temperature measuring circuit includes a thermistor and diode in parallel and a reference resistor.

10. An apparatus for measuring properties of gases being supplied to a patient according to claim 9 wherein said thermistor and said diode are located at the end of said delivery conduit near to said patient and said reference resistor is included in said gases supply.

11. An apparatus for measuring properties of gases being supplied to a patient according to claim 1 wherein said gases supply includes a device to supply gas flow, such as a blower, and a humidifier to humidify said gases from said blower.

12. An apparatus for measuring properties of gases being supplied to a patient according to claim 1 wherein said gases supply is a humidifier.

13. An apparatus for measuring properties of gases being supplied to a patient according to claim 1 wherein said electrical circuit includes a gases property measuring component.

14. An apparatus for measuring properties of gases being supplied to a patient according to claim 13 wherein said gases property measuring component includes at least one of a sensor, band pass filter or thermistor and at least one reference resistor.

15. An apparatus for measuring properties of gases being supplied to a patient according to claim 14 wherein said at least one of a sensor, band pass filter or thermistor are located at the end of said delivery conduit near to said patient and said at least one reference resistor and at least one band pass filter is included in said gases supply.

16. An apparatus for measuring a property of gases being supplied to a patient, the apparatus comprising a conduit having a proximal end and a distal end, the proximal end adapted to connect to a source of breathing gases and a distal end adapted to connect to a patient interface, the conduit comprising a wall defining a lumen, a heating wire extending from a proximal portion of the conduit to a distal portion of the conduit, a gases property sensor being positioned at the distal portion of the conduit, the gases property sensor being connected in series with the heating wire, and the gases property sensor being connected in parallel with a diode such that current flow in one direction can be used for generating heat in the heating wire and current flow in an opposite direction can be used for measuring the property of the breathing gases.

17. The apparatus of claim 16, wherein a connection to the heating wire, the gases property sensor and the diode are interconnected and sealed at a location exposed to the lumen of the conduit.

18. The apparatus of claim 16, wherein the gases property sensor comprises a thermistor that is in series with a reference resistor.

19. The apparatus of claim 18, wherein the gases property sensor comprises impedance for pressure or humidity measurement.

20. The apparatus of claim 18 in combination with a control system, the control system being configured to correlate a specific gases property sensor to a specific conduit such that the control system can apply an appropriate control strategy based upon the identified conduit.

21. An apparatus for measuring properties of gases being supplied to a patient comprising:
a gases supply,
at least one delivery conduit including a heater wire for heating said conduit,
said heater wire being located within, around or throughout said conduit and being utilised in an electrical circuit to determine said properties of said gases, said electrical circuit including a sensing means with known properties at ambient temperature such that said sensing means can be matched with said at least one delivery conduit, and
said electrical circuit providing feedback to a controller when said properties of said gases vary.

22. An apparatus for measuring properties of gases being supplied to a patient according to claim 21 wherein said sensing means is a temperature sensor.

23. An apparatus for measuring properties of gases being supplied to a patient comprising:
a gases supply,
at least one delivery conduit including a heater wire for heating said conduit,
said heater wire being located within, around or throughout said conduit and being utilised in an electrical circuit to determine said properties of said gases, said electrical circuit including at least one gas properties measuring means in series with said heater wire, said at least one gas properties measuring circuit comprising a temperature measuring circuit, said temperature measuring circuit including a thermistor and diode in parallel and a reference resistor, and
said electrical circuit providing feedback to a controller when said properties of said gases vary.

24. An apparatus for measuring properties of gases being supplied to a patient according to claim 23 wherein said thermistor and said diode are located at the end of said delivery conduit near to said patient and said reference resistor is included in said gases supply means.

25. An apparatus for measuring properties of gases being supplied to a patient comprising:
a gases supply,
at least one delivery conduit including a heater wire for heating said conduit,
said heater wire being located within, around or throughout said conduit and utilised in an electrical circuit that includes a gases property measuring means that includes at least one of a sensor, a band bass filter, or a thermistor and at least one reference resistor to determine said properties of said gases, said at least one of a sensor, band pass filter or thermistor are located at the end of said delivery conduit near to said patient and said at least one reference resistor and at least one band pass filter is included in said gases supply means and
said electrical circuit providing feedback to a controller when said properties of said gases vary.

26. An apparatus for measuring properties of gases being supplied to a patient according to claim 1, wherein said heater wire and said electrical circuit are connected in series.

27. An apparatus for measuring properties of gases being supplied to a patient according to claim 26, wherein said electrical circuit is positioned on a circuit board or a housing that is positioned in a flow of gases through said conduit.

28. An apparatus for measuring properties of gases being supplied to a patient according to claim 27, wherein said circuit board is at least partially positioned within a wall of said conduit.

29. An apparatus for measuring properties of gases being supplied to a patient according to claim 26, wherein a heating voltage is applied to said heater wire to generate heat and said heating voltage is applied and removed, said circuit being electrical powered when said heating voltage is removed.

30. An apparatus for measuring properties of gases being supplied to a patient according to claim 26, wherein a heating signal and a measurement signal can be passed along said heater wire to create a heating current and a measurement current in said heater wire, said measurement current communicating with said electrical circuit.

* * * * *